(12) United States Patent
Nakada et al.

(10) Patent No.: US 8,398,005 B2
(45) Date of Patent: Mar. 19, 2013

(54) ELECTROSTATIC ATOMIZING DEVICE

(75) Inventors: Takayuki Nakada, Hikone (JP);
Takahiro Miyata, Hirakata (JP);
Hiroshi Suda, Takatsuki (JP); Yukiyasu Asano, Kobe (JP); Masaharu Machi, Shijonawate (JP)

(73) Assignee: Panasonic Corporation, Osaka (JP)

( * ) Notice: Subject to any disclaimer, the term of this patent is extended or adjusted under 35 U.S.C. 154(b) by 157 days.

(21) Appl. No.: 12/918,639

(22) PCT Filed: Feb. 17, 2009

(86) PCT No.: PCT/JP2009/052668
§ 371 (c)(1),
(2), (4) Date: Aug. 20, 2010

(87) PCT Pub. No.: WO2009/107513
PCT Pub. Date: Sep. 3, 2009

(65) Prior Publication Data
US 2010/0327089 A1    Dec. 30, 2010

(30) Foreign Application Priority Data
Feb. 26, 2008    (JP) ................. 2008-044849

(51) Int. Cl.
*B05B 5/00*    (2006.01)
(52) U.S. Cl. .............. 239/690; 239/302; 239/690.1; 239/708
(58) Field of Classification Search .......... 239/690, 239/690.1, 302, 379, 708
See application file for complete search history.

(56) References Cited

U.S. PATENT DOCUMENTS

| | | | |
|---|---|---|---|
| 7,473,298 B2 | 1/2009 | Suda et al. | |
| 7,494,532 B2 | 2/2009 | Azukizawa et al. | |
| 7,621,470 B2 | 11/2009 | Yamaguchi et al. | |
| 7,874,503 B2 | 1/2011 | Imahori et al. | |
| 2006/0131449 A1 | 6/2006 | Azukizawa et al. | |
| 2006/0214020 A1 | 9/2006 | Suda et al. | |
| 2007/0119993 A1 | 5/2007 | Yamaguchi et al. | |
| 2009/0001200 A1 | 1/2009 | Imahori et al. | |
| 2009/0114747 A1 | 5/2009 | Nakada et al. | |
| 2009/0127357 A1* | 5/2009 | Suda et al. .............. 239/704 |
| 2009/0184186 A1 | 7/2009 | Suda et al. | |
| 2010/0001105 A1* | 1/2010 | Obata et al. .............. 239/690 |

FOREIGN PATENT DOCUMENTS

| | | |
|---|---|---|
| CN | 1802219 A | 7/2006 |
| CN | 1898027 A | 1/2007 |
| CN | 1938103 A | 3/2007 |

(Continued)

OTHER PUBLICATIONS

International Search Report for the Application No. PCT/JP2009/052668 mailed Mar. 24, 2009.

(Continued)

*Primary Examiner* — Steven J Ganey
(74) *Attorney, Agent, or Firm* — McDermott Will & Emery LLP

(57) ABSTRACT

The electrostatic atomizing device includes a discharge electrode, an opposed electrode, and a voltage application device. The voltage application device is configured to apply a voltage between the discharge electrode and the opposed electrode so as to atomizing a liquid supplied to the discharge electrode. The electrostatic atomizing device further includes a reduced water provision device configured to supply reduced water as the above liquid to the discharge electrode.

2 Claims, 2 Drawing Sheets

FOREIGN PATENT DOCUMENTS

| | | |
|---|---|---|
| EP | 1 666 156 A1 | 6/2006 |
| EP | 1 964 614 A1 | 9/2008 |
| JP | 2005-232015 A | 9/2005 |
| JP | 2006-95502 A | 4/2006 |
| JP | 2007-167796 A | 7/2007 |
| JP | 2007-260625 A | 10/2007 |
| TW | 200800407 | 1/2008 |
| WO | 2004-285036 A | 10/2004 |
| WO | WO2007072811 * | 6/2007 |

OTHER PUBLICATIONS

Supplementary European Search Report for the Application No. EP 09 71 5772 dated Mar. 2, 2012.

The First Office Action for the Application No. 200980106602.2 from the State Intellectual Property Office of the People's Republic of China dated Jul. 3, 2012.

* cited by examiner

ELECTROSTATIC ATOMIZING DEVICE

TECHNICAL FIELD

The present invention is directed to an electrostatic atomizing device which generates a mist of charged minute water particles by causing an electrostatic atomizing phenomenon.

BACKGROUND ART

In the past, as disclosed in Japanese laid-open patent publication No. 2007-167796, there is known an electrostatic atomizing device configured to atomize water (e.g. tap water) to generate a mist of charged minute water particles of nanometer size.

The aforementioned mist of charged minute water particles includes a radical such as a hydroxy radical. Such radical possesses an oxidation action. Therefore, the electrostatic atomizing device is capable of producing such as a deodorization effect, a virus and/or mold filtration effect, and a virus and/or mold suppression effect.

For example, the above Japanese laid-open patent publication discloses the charged minute water particles is attached to and is percolated into a food product to make a sterilization, a deodorizing, a degradation of harmful materials, or a moisture retention (in short, a food preservation).

Notably, objects (e.g. food products) can be deteriorated by not only action of a bacteria but also oxidization. In particular, to prevent a deterioration caused by oxidization is necessary for preserving freshness of food products for a long time.

However, the mist of charged minute water particles generated from water fails to suppress or prevent the deterioration caused by oxidization. That is, the conventional electrostatic atomizing device is incapable of preventing oxidization.

DISCLOSURE OF INVENTION

In view of the above insufficiency, the present invention has been aimed to propose an electrostatic atomizing device capable of suppressing and preventing oxidization.

The electrostatic atomizing device in accordance with the present invention includes a discharge electrode and a potential applying means. The potential applying means is configured to apply an electrical potential to the discharge electrode to atomize a liquid supplied to the discharge electrode. The electrostatic atomizing device further includes a reduced water providing means configured to supply reduced water as the liquid to the discharge electrode.

According to this invention, the mist of charged minute water particles is produced from the reduced water. The mist of charged minute water particles produced from the reduced water has a reduction action. Therefore, it is possible to suppress and prevent oxidization of a targeted object (in particular, oxidization caused by an oxidized radical contained in the mist of charged minute water particles). Thus, the electrostatic atomizing device is capable of suppressing and preventing a deterioration of the targeted object.

In a preferred embodiment, the reduced water providing means includes a water storage tank configured to store the reduced water and a liquid transporter configured to transport the reduced water stored in the water storage tank to the discharge electrode.

According to this embodiment, it is possible to provide a simplified structure of supplying the reduced water to the discharge electrode.

In a preferred embodiment, the reduced water is defined to contain a material which has a reduction action and is dissolved or dispersed in the form of a minute particle in the reduced water. The discharge electrode is formed to have at least one part made of the material. The reduced water providing means is defined by a water providing means, the discharge electrode, and the potential applying means. The water providing means is configured to supply water to the discharge electrode. The potential applying means is configured to apply the electrical potential to the discharge electrode to dissolve the material from the discharge electrode in the water supplied by the water provision unit and held by the discharge electrode or to disperse in the form of the minute particle the material from the discharge electrode in the water supplied by the water provision unit and held by the discharge electrode.

According to this embodiment, the reduced water is generated by dissolving the material forming at least one part of the discharge electrode in the water supplied to the discharge electrode or by dispersing in the form of the minute particle the material forming at least one part of the discharge electrode in the water supplied to the discharge electrode. Therefore, the reduced water need not be prepared. Further, it is possible to provide a simplified structure of supplying the reduced water to the discharge electrode.

In addition, the material is preferred to be platinum.

BEST MODE FOR CARRYING OUT THE INVENTION (First Embodiment)

Figure 1:
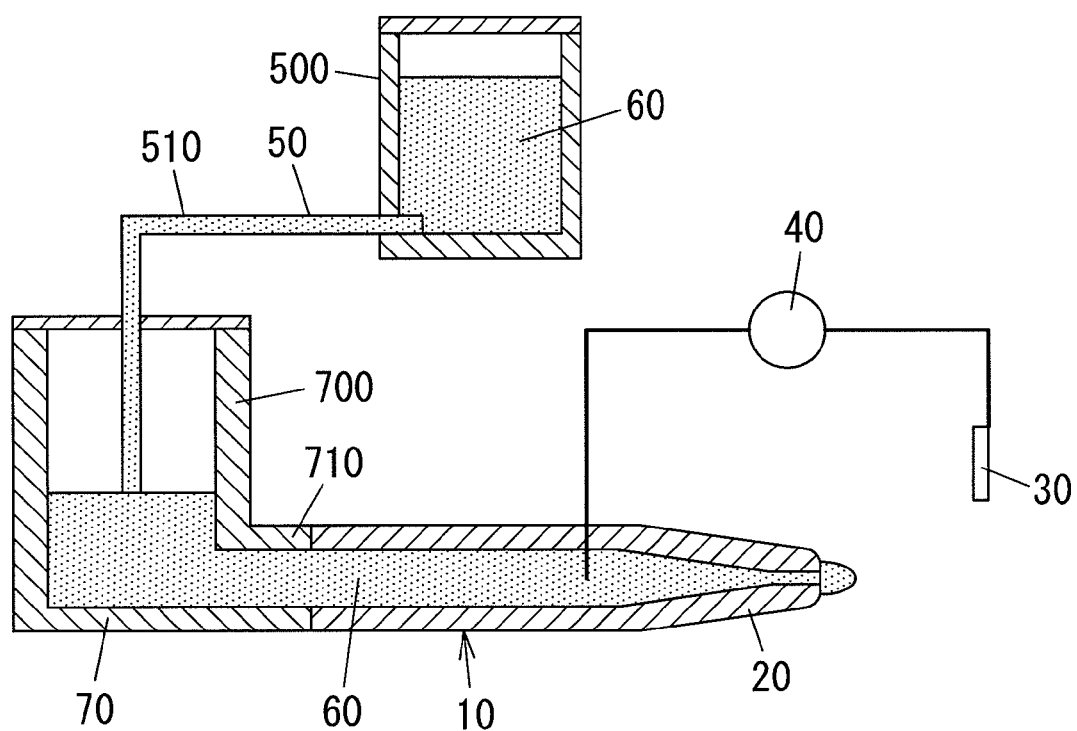
FIG. 1 is a schematic view illustrating an electrostatic atomizing device in accordance with a first embodiment.

FIG. 1 shows an electrostatic atomizing device 10 which includes a discharge electrode (atomizing electrode) 20, an opposed electrode 30, and a voltage application device (voltage applying means) 40. The electrostatic atomizing device 10 further includes a reduced water provision device (reduced water providing means) 50 configured to have the discharge electrode 20 hold reduce water 60.

The discharge electrode 20 is made of metals and is shaped into a cylindrical shape (e.g. a circular cylindrical shape). The discharge electrode 20 has its front end portion (right end portion, in FIG. 1) which has its inner diameter made smaller towards its front end than at its rear end. The inner diameter at the front end of the discharge electrode 20 is selected such that the reduced water 60 outside the front end of the discharge electrode 20 can be kept in a spherical shape by its surface tension. In short, the reduced water 60 is prevented from flowing out from the front end of the discharge electrode 20. Therefore, the reduced water 60 is held at the front end of the discharge electrode 20.

In the electrostatic atomizing device 10 of the present embodiment, the discharge electrode 20 is attached to a reservoir 70. The reservoir 70 includes a reservoir body 700, for example. The reservoir body 700 is provided with a supply conduit 710 on a lower portion of its side surface. The supply conduit 710 has its inside communicate to an inside of the reservoir body 700, and the reduced water 60 in the reservoir body 700 flows outside through the supply conduit 710. The discharge electrode 20 is attached at an apex of the supply conduit 710. Therefore, the reduced water 60 in the reservoir body 710 is supplied to an inside of the discharge electrode 20 through the supply conduit 710.

The reduced water provision device 50 includes a tank 500 and a cylindrical-shaped liquid transporter 510, and the tank 500 is a water storage tank configured to store the reduced water 60. The liquid transporter 510 is configured to connect the tank 500 to the reservoir body 700. The liquid transporter 510 acts as water distributing pipe for distributing the reduced water. Namely, the reduced water 60 stored in the tank 500 is transported to the reservoir body 700 via the liquid transporter 510. The reduced water 60 in the reservoir body 700 flows into the discharge electrode 20 via the supply conduit 710. As apparent from the above, the liquid transporter 510 is configured to transport the reduced water 60 stored in the tank 500 to the discharge electrode 20. The illustrated instance shows the reduced water provision device 50 which utilizes gravity to supply the reduced water 60 to the discharge electrode 20. However, the reduced water provision device 50 may be configured to utilize such as capillarity and a pump to supply the reduced water 60 to the discharge electrode 20.

The voltage application device 40 is configured to apply a voltage between the discharge electrode 20 and the opposed electrode 30. For example, the voltage application device 40 is a high voltage application device (high voltage applying means) configured to apply a voltage (e.g. voltage of 5000V) enough to atomize the reduced water 60 between the discharge electrode 20 and the opposed electrode 30 by use of an electrical power received from a commercial AC power source. The voltage application device 40 can be made by use of well known techniques and no detailed explanation is deemed necessary. It is noted that the voltage application device 40 of the present embodiment is configured to apply a negative potential to the discharge electrode 20 and to apply a ground potential (0V) to the opposed electrode 30. In the present embodiment, the voltage application device 40 functions as a potential applying means configured to apply an electrical potential to the discharge electrode 20 to atomize the liquid supplied to the discharge electrode 20. The voltage application device 40 need not apply the ground potential to the opposed electrode 30. The opposed electrode 30 may be grounded instead of being supplied with the ground potential from the voltage application device 40. In this case, the voltage application device 40 is configured to apply an electrical potential to the discharge electrode 20 only. The opposed electrode 30 can be replaced by a part of a housing (not shown) configured to house the electrostatic atomizing device 10 or a part of a main body (not shown) of an instrument to which the electrostatic atomizing device 10 is attached. In short, if the part of the housing or the main body is grounded, the electrostatic atomizing device 10 is not required to involve the opposed electrode 30. Thus, it is possible to simplify a configuration of the electrostatic atomizing device 10.

The opposed electrode 30 is opposed to the front end of the discharge electrode 20 and is spaced from the discharge electrode 20 by a predetermined distance. A distance between the discharge electrode 20 and the opposed electrode 30 is appropriately selected according to a usage pattern of the electrostatic atomizing device 10. Further, the opposed electrode 30 is not required to be opposed to the discharge electrode in a strict sense. In brief, the opposed electrode 30 is allowed to be arranged such that the atomization of the reduced water 60 held by the discharge electrode 20 is successfully made by applying the voltage between the discharge electrode 20 and the opposed electrode 30.

In the electrostatic atomizing device 10 of the present embodiment, for the purpose of generating the mist of charged minute water particles, the voltage application device 40 applies the voltage between the discharge electrode 20 and the opposed electrode 30 while the discharge electrode 20 has the reduced water 60 at its front end. Thereby, a Coulomb force acts on the reduced water 60 because an electric field is impressed to the reduced water 60 at the front end of the discharge electrode 20. The Coulomb force causes the surface of the reduced water 60 to bulge locally, thereby forming a Taylor cone. Then, electric charges become concentrated at a tip of the Taylor cone to increase the electric field intensity and therefore the Coulomb force, thereby further developing the Taylor cone. Energy (repulsion caused by high-density charges) which acts on the reduced water 60 at the tip of the Taylor cone becomes high as charge density at the tip of the Taylor cone becomes high. Accordingly, upon the charge density at the tip of the Taylor cone exceeding a predetermined value, the Coulomb force exceeds the surface tension of the reduced water 60. Thereby, the reduced water 60 is caused to disintegrate repeatedly (Rayleigh disintegration) to generate a large amount of the mist of charged minute water particles of nanometer sizes. The mist of charged minute water is charged positively or negatively.

Water in which a material (hereinafter called "reducing material", in the first and second embodiment) having a reduction action is dispersed in the form of a solid, minute particle can be adopted as the reduced water 60. In addition, water in which the reducing material is dissolved can be adopted as the reduced water 60. Herein, the reducing material is not limited to a material generally referred to as a reductant having reducing ability by itself. For example, the reducing material can be broadly defined as a material (e.g. platinum nano-size particle) which functions as a catalyst to quench active oxygen.

In the present embodiment, water in which a platinum minute particle is dispersed is adopted as the reduced water 60. A platinum nano-size particle (e.g. a platinum minute particle of 2 nm size) is adopted as the platinum minute particle. To electrostatically atomize this reduced water 60 generates the charged minute water particles of nanometer size which includes the platinum nano-size particle. Preferably, the charged minute particles include those particles of nanometer size which are distributed to show a peak in a particle size range of 15 to 30 nm.

Such the charged minute water particle is of nanometer size and is extremely small. Therefore, the charged minute water particles are delivered far and wide. After the charged minute water particles come into contact with a surface of a targeted object (e.g. a food, a skin, and a hair), the charged minute water particles percolate into the target object. Therefore, the charged minute water particle can deliver the platinum nano-size particle to an inside of the targeted object.

Although platinum is not a reductant in a strict sense, it is well known that the platinum nano-size particle produces an effect of catalytically quenching the active oxygen (that is, the platinum nano-size particle acts as a catalyst to bring about the reduction action). Therefore, on the surface or in the inside of the targeted object, the platinum nano-size particle functions as the catalyst for reduction. Accordingly, when the water in which the platinum nano-size particles are dispersed is adopted as the reduced water 60, it is possible to prevent the targeted object from being oxidized. In particular, in the case of the targeted object being a food, it is possible to prevent not only a surface of the food but also an inside of the food from being oxidized. Thus, the freshness of the food can be preserved.

In the case of the targeted object being a skin and/or hair, the platinum nano-size particle suppresses the oxidization on a surface of the skin and/or hair and/or in an inside of the skin and/or hair. That is, the platinum nano-size particle can prevent the skin and hair from being deteriorated (aged). Further, the charged minute water particle of nanometer size containing the platinum nano-size particle goes into an inside of the body via the mouth or nose. In this case, it is possible to suppress the aging because the platinum nano-size particle suppresses the oxidization inside the body.

It is noted that the reduced water 60 is not limited to the water in which the platinum nano-size particles are dispersed. For example, water in which a material having the reduction action but platinum is dispersed can be adopted as the reduced water 60. In addition, the reduced water 60 can be selected from such as hydrogen water (active hydrogen water) and ascorbic acid water. It is noted that the hydrogen water means water containing a large amount of hydrogen.

In the case of the hydrogen water being adopted as the reduced water 60, the hydrogen water may be made by electrolysis of the water stored in the tank 500. The hydrogen water produced in the tank 500 may be transported to the front end of the discharge electrode 20 by the liquid transporter 510 and subsequently may be electrostatically atomized.

Namely, the reduced water provision device 50 may include an electrolysis device (not shown) configured to produce the hydrogen water by electrolysis of the water stored in the tank 500, in addition to the tank 500 and the liquid transporter 510. According to this configuration, the reduced water 60 can be produced in the tank 500. Therefore, it is not required to preliminarily generate the reduced water 60 by use of an external device. It is only required to supply water to the tank 500.

To electrostatically atomizing the hydrogen water and the ascorbic acid water produces a mist of charged minute hydrogen water particles and a mist of charged minute ascorbic acid water particles, respectively. The hydrogen water and the ascorbic acid water are the reductant by themselves. Therefore, in the case of the reduced water 60 being selected from the hydrogen water and the ascorbic acid water, it is possible to suppress the deterioration caused by the oxidization because the reduced water 60 produces the reduction action on the surface or in the inside of the targeted object.

In the case of the discharge electrode 20 being supplied with water instead of the reduced water 60, the voltage applied between the discharge electrode 20 and the opposed electrode 30 generates a free radical (e.g. [.H], [.OH], and [.$O_2$]) in the water at the front end of the discharge electrode 20. In this case, an electron ($e^-$) is provided to the Taylor cone of the water from the discharge electrode 20 when the voltage is applied to give a lower potential to the discharge electrode 20 than the opposed electrode 30. Therefore, the electron combines with [.H] to produce $H_2$. As a result. [.OH] and [.$O_2$] remain in the water. Finally, the electrostatically atomization produces the charged minute water particle containing active oxygen. This negatively-charged minute water particle is defined to contain the active oxygen such as [.OH] and [.$O_2$].

Figure 2:
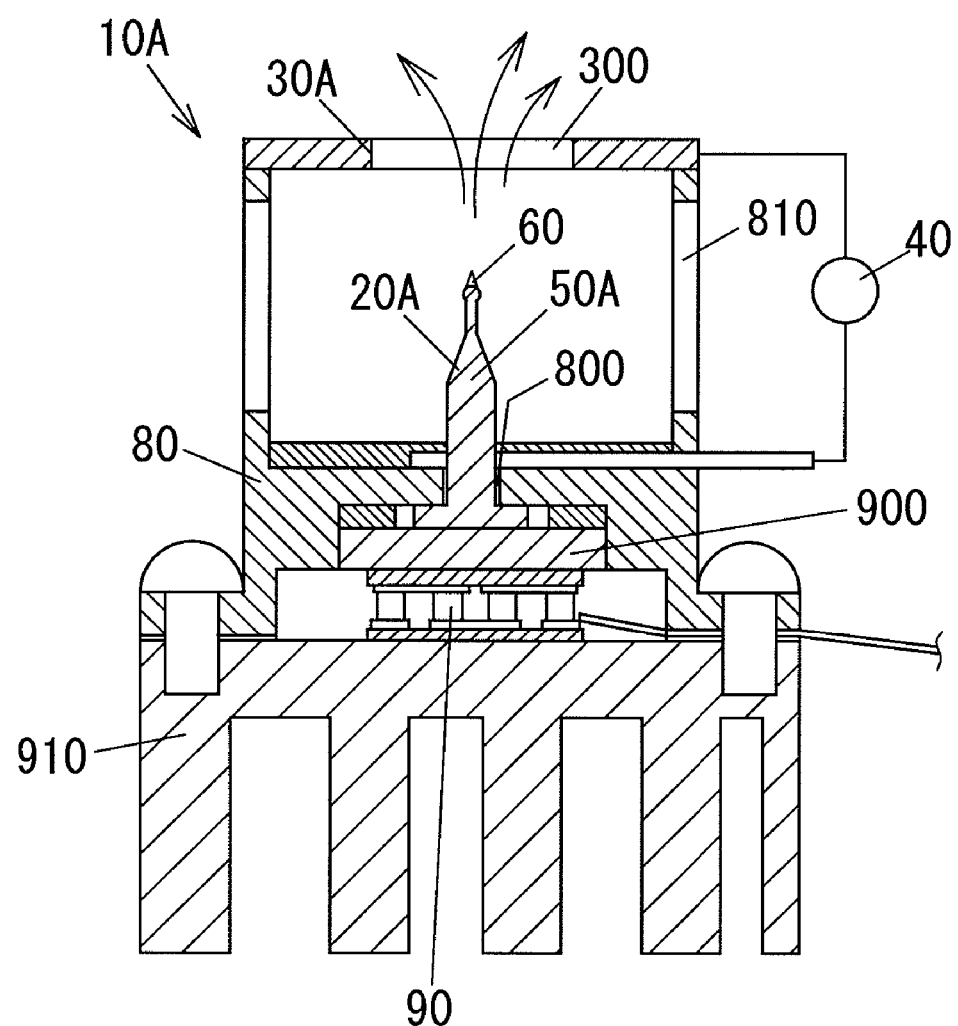
FIG. 2 is a schematic view illustrating an electrostatic atomizing device in accordance with a second embodiment.

By contrast, the electrostatic atomizing device 10 in accordance with the present embodiment generates the mist of the charged minute water particles containing the material having the reduction action. Further, the reducing material contained in the charged minute water particle has enough reduction ability to supersede or prevail the oxidation caused by the oxidized radical of [.OH] and [$O_2$] contained in the charged minute water particle. Therefore, the oxidized radical of [.OH] and [$.O_2$] is prevented from producing the oxidation action, and the reduction action caused by the reducing material suppresses the oxidation.

As described in the above, the electrostatic atomizing device 10 of the present embodiment includes the discharge electrode 20, the opposed electrode 30, and the voltage application device 40. The voltage application device 40 is configured to apply a voltage between the discharge electrode 20 and the opposed electrode 30 to atomize a liquid held by the discharge electrode 20. The electrostatic atomizing device 10 further includes the reduced water provision device 50 configured to supply the reduced water 60 as the liquid to the discharge electrode 20.

According to the electrostatic atomizing device 10, the mist of charged minute water particles is produced from the reduced water 60. Unlike charged minute water particle produced from mere water such as tap water, the charged minute water particle produced from the reduced water 60 has the reduction action. Therefore, it is possible to suppress and prevent oxidization of a targeted object (in particular, oxidization caused by an oxidized radical contained in the mist of charged minute water particles). Thus, the electrostatic atomizing device is capable of suppressing and preventing a deterioration of the targeted object.

In addition, the reduced water provision device 50 includes the tank 500 configured to store the reduced water 60 and the liquid transporter 510 configured to transport the reduced water 60 stored in the tank 50 to the discharge electrode 20. Accordingly, it is possible to provide a simplified structure of supplying the reduced water 60 to the discharge electrode 20. In addition, it is possible to generate the charged minute water particle containing a minute particle having the reduction action irrespective of a material of the discharge electrode 20.

Further, when the reduced water 60 is water having the reducing material dispersed therein, the reducing material floats in air in a state of being contained in the tiny charged minute water particle and comes into contact with the target. The charged minute water particle percolates into the targeted object because the charged minute water particle is tiny. Further, the charged minute water particle goes into the inside of the body via the mouth or nose. After the mist of the charged minute water particle is evaporated, the reducing material produces the reduction action on the surface or the inside of the targeted object and particularly suppresses the oxidization caused by the oxidized radical contained in the charged minute water particle. Accordingly, it is possible to suppress and prevent the oxidization of the targeted object. Thus, the deterioration of the oxidization of the targeted object can be suppressed and prevented. Further, in contrast to a situation where the reducing material alone flies and adhere to the target, the reduction due to the reducing material can be delayed by a time during which the water (charged minute water particles) is evaporated. Whereby, the reducing material can achieve the reduction only after it adheres and permeated into the target. Thus, the oxidization can be successfully suppressed and prevented by the reducing material.

(Second Embodiment)

As shown in FIG. 2, the electrostatic atomizing device 10A of the present embodiment includes the discharge electrode 20A, the opposed electrode 30A, the voltage application device 40, a housing 80, and a cooler 90. Since the voltage application device 40 is the same as that of the first embodiment 1, the voltage application device 40 is designated by the same reference number and no explanation is deemed necessary.

The discharge electrode 20A is shaped into a column shape, for example. The discharge electrode 20A has its outer diameter made smaller towards its front end than at its rear end. The discharge electrode 20A is made of the reducing material. For example, the reducing material can be selected from platinum (Pt), zinc (Zn), silver (Ag), and titanium (Ti).

The housing 80 is shaped into a box shape which having its entire first surface (upper surface, in FIG. 2) opened. The housing 80 is provided in its second surface (lower surface, in FIG. 2) with a communication hole 800 communicating an inside of the housing 80 with an outside of the housing 80. The discharge electrode 20A has its front end inserted into the housing 80 via the communication hole 800. The housing 80 is provided with window holes 810 in its side surface. The window 810 is provided to the housing 80 for introducing circumambient air into the housing 80.

The opposed electrode 30A is disposed on the first surface of the housing 80. The opposed electrode 30A is shaped into a plate shape having enough dimensions to cover an opening in the first surface of the housing 80. Further, the opposed electrode 80 is provided with a spray hole 300 extending along its thickness direction. The spray hole 300 is designed for discharging the charged minute water particles produced in the housing 80 to the outside of the housing 80.

The cooler 90 is adapted to cool the discharge electrode 20A. The cooler 90 is a peltier unit 90 which includes a peltier module 900 and a heat dissipation fin 910 configured to contact with a heater region of the peltier module 900. The cooler 90 is attached to the second surface of the housing 80 such that the peltier module 900 has its cooler region contacting with the rear end of the discharge electrode 20A. The cooler 90 is driven to cool the discharge electrode such that the temperature of the discharge electrode 20A becomes not greater than a dew point temperature of circumambient air. When the discharge electrode 20A is cooled below the dew point temperature, moisture in the circumambient air is condensed on the surface of the discharge electrode 20A. Therefore, dew is produced on the surface of the discharge electrode 20A. That is, the cooler 90 is configured to supply water (dew condensation water) to the discharge electrode 20A utilizing dew condensation (surface condensation). As apparent from the above, the cooler 90A functions a water supplying means configured to supply water to the discharge electrode 20A.

When the relatively high voltage (high voltage) is applied across the discharge electrode 20A and the opposed electrode 30A, the resulting energy given by the high voltage is likely to dissolve a part of the discharge electrode 20A held in contact with the water or separate the same from the discharge electrode 20A in the form of the minute particle. As a result, the water held by the discharge electrode 20A is changed into the reduced water 60 containing the reducing material. In addition, corona discharge brings about separation of a part of the discharge electrode 20A held in no contact with the water from the discharge electrode 20A. This minute particle is dispersed into the water held by the discharge electrode 20A. As a result, the water held by the discharge electrode 20A is changed into the reduced water 60 containing the reducing material.

Namely, in the electrostatic atomizing device 10A, a reduced water provision device (reduced water providing means) 50A is defined by the discharge electrode 20A, the voltage application device 40, and the cooler 90. The reduced water provision device 50A is configured to apply a voltage between the discharge electrode 20A and the opposed electrode 30A (In other words, the electrical potential applied to the discharge electrode 20A) to dissolve or disperse in the form of the minute particle the material of the discharge electrode 20A in the water supplied to the discharge electrode 20A by use of the cooler 90.

In the electrostatic atomizing device 10A, in order to generate the charged minute water particles, first the cooler 90 is driven to cool the discharge electrode 20A to generate the dew on the surface of the discharge electrode 20A. Subsequently, the voltage application device 40 is driven to apply the voltage between the discharge electrode 20A and the opposed electrode 30A. The Taylor cone is formed from the water held by the discharge electrode 20A when a voltage (high voltage) not less than a predetermined voltage is applied between the discharge electrode 20A and the opposed electrode 30A. Further, the reducing material is dissolved in the Taylor cone. Alternatively, the reducing material is separated from the discharge electrode 20A and is dispersed into the Taylor cone in the form of the minute particle. Therefore, the Taylor cone contains the reducing material.

Especially, the resulting energy given by the applied high voltage is likely to dissolve a part of the discharge electrode 20A held in contact with the water or separate the same from the discharge electrode 20A in the form of the minute particle. Therefore, the Taylor cone from the reduced water 60 containing the reducing water is produced.

In addition, corona discharge brings about separation of the reducing material composing a part of the discharge electrode 20A held in no contact with the Taylor cone from the discharge electrode 20A. This minute particle is dispersed into the Taylor cone when coming into contact with the Taylor cone. Therefore, the Taylor cone from the reduced water 60 containing the reducing water is produced.

Accordingly, the charged minute water particle containing the reducing material is produced by electrostatically atomizing this Taylor cone.

As described in the above, according to the electrostatic atomizing device 10A, the reduced water 60 is generated by dissolving the material forming the discharge electrode 20A in the water supplied to the discharge electrode 20A or by dispersing in the form of the minute particle the material forming the discharge electrode 20A in the water supplied to the discharge electrode 20A. Therefore, the reduced water 60 need not be prepared. Further, it is possible to provide a simplified structure of supplying the reduced water 60 to the discharge electrode 20A.

Herein, when the discharge electrode 20A is made of platinum, the water in which the platinum nano-size particle is dispersed is produced as the reduced water 60.

Although the present embodiment exemplifies an instance where the entire discharge electrode 20A is made of the reducing material, the discharge electrode 20A may have at least one part (especially, a surface part coming into contact with moisture) made of the reducing material. In the present embodiment, the water supplying means is the pettier unit 90 configured to cool the discharge electrode 20A. However, the water supplying means may be a water provision device configured to supply water stored in a water tank to the front end of the discharge electrode 20A by use of a transporting means. It is noted that the transporting means may be a device utilizing capillarity. In the present embodiment, the pettier unit 90 cools directly the discharge electrode 20A to produce the dew on the surface of the discharge electrode 20A. Alternatively, the dew may be produced on a surface of a cooling member (not shown) which is provided as separated parts from the discharge electrode 20A by use of a cooling means such as the pettier unit 90. In this case, the dew generated on the cooling member by dew condensation may be transported to the discharge electrode 20A by the transporting means.

The invention claimed is:

1. An electrostatic atomizing device comprising:
   a discharge electrode;
   a potential applying device configured to apply an electrical potential to said discharge electrode to atomize a liquid supplied to said discharge electrode; and
   a reduced water providing device configured to supply reduced water as said liquid to said discharge electrode, wherein the reduced water is defined to contain a material which has a reduction action and is dissolved or dispersed in the form of a minute particle in the reduced water, said discharge electrode being formed to have at least one part made of said material, said reduced water providing device being defined by a water providing unit, said discharge electrode, and said potential applying device, said water providing unit being configured to supply water to said discharge electrode, and said potential applying device being configured to apply the electrical potential to said discharge electrode to dissolve or disperse in the form of the minute particle the material of said discharge electrode in the water supplied by said water providing unit and supplied to said discharge electrode.

2. An electrostatic atomizing device as set forth in claim 1, wherein
said material is platinum.

* * * * *